United States Patent [19]

Waldstein

[11] 4,176,076

[45] * Nov. 27, 1979

[54] MONOALKANOLAMIDE BORATES, COMPOSITIONS CONTAINING THE SAME, AND THE USE THEREOF AS RUST-INHIBITORS AND AS SYNERGISTIC LUBRICATIVE-ENHANCIVE ADDENDA

[76] Inventor: David A. Waldstein, 622 Bergen Ave., Jersey City, N.J. 07304

[*] Notice: The portion of the term of this patent subsequent to Jul. 13, 1993, has been disclaimed.

[21] Appl. No.: 850,132

[22] Filed: Nov. 10, 1977

Related U.S. Application Data

[60] Continuation-in-part of Ser. No. 674,322, Apr. 7, 1976, abandoned, which is a division of Ser. No. 450,565, Mar. 13, 1974, Pat. No. 3,969,236.

[51] Int. Cl.$^2$ ............................................. C10M 1/10
[52] U.S. Cl. .................................. 252/49.6; 252/33.6; 252/34; 252/49.5; 252/75; 252/78.1

[58] Field of Search ...................... 252/33.6, 34, 49.5, 252/49.6, 75, 78.1, 389 R; 260/55 B

[56] References Cited

U.S. PATENT DOCUMENTS

| | | | |
|---|---|---|---|
| 3,969,236 | 7/1976 | Waldstein | 252/49.5 |
| 4,022,713 | 5/1977 | Waldstein | 252/33.6 X |

*Primary Examiner*—Delbert E. Gantz
*Assistant Examiner*—Andrew Metz
*Attorney, Agent, or Firm*—Kirschstein, Kirschstein, Ottinger & Cobrin

[57] ABSTRACT

As novel compounds, monoalkanolamide borates having from 2 to 3 carbon atoms in the alkanol moiety and in which the moiety is substituted or unsubstituted, a method for making and using the same, and the use thereof as rust-inhibitors and as synergistic lubricative-enhancive addenda. The new compounds also have bactericidal and fungicidal properties.

1 Claim, No Drawings

4,176,076

MONOALKANOLAMIDE BORATES, COMPOSITIONS CONTAINING THE SAME, AND THE USE THEREOF AS RUST-INHIBITORS AND AS SYNERGISTIC LUBRICATIVE-ENHANCIVE ADDENDA

CROSS REFERENCE TO RELATED APPLICATIONS

This application is a continuation-in-part of application Ser. No. 674,322 filed Apr. 7, 1976, now abandoned which is a divison of application Ser. No. 450,565 filed Mar. 13, 1974, now U.S. Pat. No. 3,969,236.

1. Field of the Invention

Monoalkanolamide borates, their method of manufacture and compositions of matter containing the same.

2. Description of the Prior Art

The present invention is addressed primarily to the provision of novel rust-inhibitors, although the new inhibitors have been observed to have secondary functions of considerable importance such as synergistically increasing the lubricity of compounds with low lubricity and acting as bactericides and fungicides.

The rust-inhibitor most commonly used heretofore was sodium nitrite ($NaNO_2$). Typically it was employed as an addendum for liquids that during their intended utilization contacted ferrous surfaces. These liquids included water, cutting oils, grinding oils, pentrating oils, drawing oils, iron-tinning oils, hydraulic oils, oil-in-water and water-in-oil emulsions, synthetic and semi-synthetic metal-working fluids, paints, varishes and adhesives.

However, sodium nitrite is a carcinogen, so that, although when employed for the purposes mentioned, it was not ingested and, if care was taken, it did not contact people's skin, it presented, nevertheless, a potential hazard which could be avoided if a suitable substitute therefor could be found. Furthermore, for various reasons, the presence of sodium nitrite is ecologically undesirable in sewer wastes and in discharges into bodies of water.

SUMMARY OF THE INVENTION

1. Purposes of the Invention

It is an object of this invention to provide new compounds to wit, monoalkanolamide borates having from 1 to 3 carbon atoms in the alkanol moiety and in which said moiety is substituted or unsubstituted.

It is another object of the invention to provide new compounds which are the reaction products of orthoboric acid with monoalkanolamines having from 1 to 3 carbon atoms in the alkanol moiety and in which said moiety is substituted or unsubstituted, the reaction being carried out at a mild temperature and the water produced by the reaction optimally being removed.

It is another object of the invention to provide novel rust inhibitors, to wit, monoalkanolamide borates of the character described, which are oil and water soluble and therefore can be incorporated readily in all classes of liquids.

It is another object of the invention to provide novel compounds, to wit, monoalkanolamide borates of the character described, which, in addition to a primary rust-inhibiting function, synergistically enhance lubricity of semi-lubricious and lubricious compounds and compositions, improve surface finish of ferrous articles being ground, are effective bactericides and fungicides, can be discharged into sewers, drains and large bodies of water without ecological damage and are not carcinogeneous.

It is another object of the invention to provide compositions embodying the aforesaid rust-inhibiting compounds and a carrier which later simply may be a diluent and which, optionally, may have some other major function, e.g. lubricating or film-forming.

It is another object of the invention to provide a method of lubricating a surface and of inhibiting rusting of a ferrous surface by use of the aforesaid compounds.

It is another object of the invention to provide novel rust-inhibiting compounds which are inexpensive to make, easy to incorporate in a carrier, non-toxic upon ingestion or dermal contact and are effective for their primary purpose, rust-inhibition, in low concentrations.

Other objects of this invention in part will be obvious and will be pointed out hereinafter.

2. Brief Description of the Invention

The principal feature of the present invention is the provision of novel compounds and the rust-inhibiting characteristic thereof. Secondary features are the ability of these compounds synergistically to increase the lubricity of semi-lubricious and lubricious compounds, to enhance the surface finish to metals during grinding and to act as bactericides and fungicides. The novel compounds are monoalkanolamide borates in which the alkanol moiety has from 1 to 3 carbon atoms and is substituted or unsubstituted. Said compounds are made by reaction of orthoboric acid with one or more monoalkanolamides having from 1 to 3 carbon atoms in the alkanol moiety and in which the alkanol moiety is substituted or unsubstituted, the reactants being present in stoichiometric proportions or with an excess of either, preferably the amine if an excess of either is used, and the reaction taking place under a mild temperature, e.g. 130° to 165° C. Wide variations in the temperature of reaction may be employed although the indicated range has been found to be most effective and most efficient. The water produced by the reaction desirably is removed as the reaction proceeds, for example by heating in a closed vessel having a reflux condensor with an external collector. Residual water can be removed by solvent extraction.

The new compounds are added to carriers to form compositions that are to be applied to surfaces and in this environment have been found to be excellent inhibitors of rust. They are effective in concentrations as low as ½% to 1% by weight of the compositions. They are particularly good for cast iron and are excellent when employed as solvents in cutting and grinding. The compositions can be used anywhere that they will be applied to ferrous rustable surfaces, e.g. the compounds in combination with cutting oils, grinding oils, penetrating oils, drawing oils, iron-trimming oils, hydraulic oils, oil-in-water emulsions, water-in-oil emulsions, synthetic and semi-synthetic metal-working fluids, paints, varnishes and adhesives.

The new compounds, which have essentially no lubricity, unexpectedly increase the lubricity of liquids having a low level of lubricity as well as liquids having a higher lever of lubricity. It is an interesting ancillary property of the new compounds that, being intended for use, as they are, with carriers such as oils and organic substances which are susceptible to bacterial and fungal attack, they will protect the oils and organic substances against these attacks. Thus the single compound—a monoalkanolamide borate—concurrently performs three functions that are mutually desirable in the fields in which the compound is used, i.e. it will inhibit rust, it will enhance lubrication and it will act as a bactericide and fungicide. This renders the new compound uniquely superior to sodium nitrite for uses such as grinding, cutting and hydraulic fluids without taking into account its non-carcinogeneous and ecologically acceptable nature.

The invention accordingly consists in the compounds, compositions of matter employing the compounds, methods of using such compositions of matter and methods of making and using the compounds which are exemplified in the compounds, compositions and methods hereinafter described and of which the scope of application will be indicated in the appended claims.

DESCRIPTION OF THE PREFERRED EMBODIMENTS

The new compounds of the present invention are monoalkanolamide borates in which the alkanol moiety has from 1 to 3 carbon atoms and is substituted or unsubstituted. Typical alkanol moieties are: monethanol, monomethanol, 1-isopropanol, mono-n-propanol and 2-amino-2-methyl propanol. The compounds are the reaction products of orthoboric acid ($H_3BO_3$) with an amine of an appropriate monoalkanol such as a monoalkanol just mentioned. If desired more than one alkanolamine can be included in the reaction in which event the reaction products will be mixtures of monoalkanolamide borates which will be useful in accordance with this invention. The reaction preferably is carried out in a closed vessel at a mild temperature and the water which is a reaction side product can be stripped off by a reflux condensor connected to the reaction vessel and having a closed external collector. Any residual water remaining can be removed by solvent extraction, as with toluene or benzene. All the water can be removed in this fashion, if desired, without use of the reflux condensor but the latter is preferred since it makes this reaction more effective and more efficient. The temperature of the reaction is not critical; too low a temperature is economically undesirable and too high a temperature is destructive. The water formed by reaction is not harmful to the reaction products; indeed, the reaction products are added to water for some uses and for sale as a concentrate. But, in general, it is preferred to remove the water both to expedite the reaction and to provide anhydrous products which, if desired, can be added to anhydrous oils for uses in compositions where water is not desired, e.g. hydraulic fluids, due to its narrow useable temperature range.

By way of example, monoisopropanolamide borate, one of the borates of the instant invention, is formed by mixing one gram mol of orthoboric acid with one and one-half gram mols of 1-isopropanolamine in a reactor open to the ambient atmosphere. The reactor has heating means and a reflux condenser with an external closed collector. The reactants are mixed to form a homogeneous mass. Then the reactor is closed and the temperature raised to between about 130° C. to about 165° C. for between about 4 to about 5 hours. During this period the water formed in the reaction condenses in the reflux condensor and is removed from the reacting mixture by desposit in the external collector. If desired the reactor can be operated under a vacuum, e.g., about 5 mm. of mercury. The details of the reaction conditions have been mentioned only by way of example, they are not to be considered as limitations; essentially the same conditions may prevail where other monoalkanolamines are used in the reactor. The amount of the monoalkanolamines employed desirably is in excess of that necessary for a stoichiometric ratio. Thus, although it has been mentioned above that $1\frac{1}{2}$ gram mols of monoisopropanol are mixed with one gram mol of orthoboric acid, and although such proportion may be employed where other alkanolamines are used in the reaction, desirable results are secured where the amount of the alkanolamine that is charged into the reactor varies from 1 to about 2 gram mols per gram mol of the orthoboric acid. Any excess of unreacted alkanolamine can be left in the reaction product (the alkanolamide borate) inasmuch as it does not interfere with the rust inhibiting action, the lubricating-enhancing action and the bactericidal and fungicidal action of the said borate.

The reaction product, i.e. the alkanolamide borate, is a clear water-white oily heavy syrup. It is freely soluble in water and also is soluble in substantially all organic liquids; e.g. oils. This makes it particularly easy to incorporate in liquid carriers for various purposes.

The alkanolamide borate desirably is present in an amount of at least 0.05% by weight of the liquid in which it is included in order for it to be effective as a rust-inhibitor, as a synergistic lubricating-enhancive addendum and as a bactericide and fungicide. For convenience, where the aforesaid borate is to be added to water, or to a liquid that includes water, e.g. an emulsion, the borate can be marketed as a water concentrate which subsequently is added to a liquid for further dilution of the borate. A satisfactory concentration in water is about 30% by volume of the alkanolamide borate.

In concentrations of between about $\frac{1}{2}$% by weight to about 1% by weight of the borate in an oil-in-water or water-in-oil emulsion the said borate acts as an excellent rust-inhibitor for ferrous metals. A preferred ratio in a coolant is about 0.8% by weight of the said borate of the coolant.

As mentioned previously, the alkanolamide borate of the invention, in addition to serving as a rust-inhibitor for ferrous metals increases the lubricity of the lubricant present, whatever it may be. It will raise the lubricity of lubricants of poor lubricity to an acceptable level and will increase the lubricity of lubricants having a higher starting lubricity. The said borates further are useful in this particular application, i.e. in oils, because oils are prone to bactericidal and fungicidal attack which are prevented by the presence of alkanolamide borates.

An alkanolamide borate of the present invention has no Falax value and therefore no lubricity; it being observed that from about zero to 2,000 on the Falax scale is equivalent to a neglible lubricity. When an alkanolamide borate of the present invention is added to a water soluble oil with a low lubricity, for example about 600 Falax, being added in the proportions above mentioned, to wit, between $\frac{1}{2}$% to 1% by weight of the water soluble oil emulsion, the resulting composition has a high lubricity of about 3,000 Falax or better; hence not only does the water soluble oil and the water with which it is mixed now have the ability to inhibit the growth of bacteria and fungi but it has the added advantage of high lubricity. This enhanced lubricity is a desirable side effect, for instance when the aforesaid oil in an emulsion also containing water is used as a coolant during cutting, the friction between the cutting tool and the metal surface is reduced which is a help in the cutting of both ferrous and non-ferrous surface. When such coolants are used for grinding and cutting metal the ensuing surface is smoother than with conventional coolants not including a borate of the present invention. This particularly is useful for the grinding of cast iron surfaces although it is also an advantage in the grinding of other ferrous and non-ferrous surfaces. One excellent application of a coolant using a borate of the invention is for grinding disc brakes. The ground surface has a fine surface finish.

By way of example, cutting oils used in connection with alkanolamide borates of the present invention include naphthene based distillate fractions. One specific oil is a mixture of refined based oil fractions having an SUS at 100° F. between 70 and 800. Another proprietary cutting oil which also can be used by way of example with a borate of this invention is sold by the Texaco Company under the trade name of Soluble Oil TL 337. Another cutting oil which can be used with said borates is a mineral lubricating oil. Other commercial cutting oils that are improved by the addition of said borates are: Trim Regular, Citgo Coolant, Vantrol, Sun Seco, Norton Wheelmate, Chemtool, Monroe Primecut and Lusol.

It is customary to have present in cutting and cooling oils, in addition to a rust-inhibiting agent for which there will be used an alkanolamide borate of this invention, other addenda such as surfactants, coupling agents and water.

Typical surfactants include:
sodium and potassium salts of:
  petroleum sulfonic acids
  naphthenic acids
  fatty acids
  rosin
  tall oil
  oil-soluble metal petroleum sulfonates
  metal naphthanates
  metal resinates
alkanolamine condensates of carboxylic acids containing
  at least 10 carbon atoms,
  ethoxylated alkyl and aryl hydroxy compounds.
All of the foregoing surfactants are emulsifiers.

Mixtures of emulsifiers, for example, a mixture of sodium naphthanate and sodium petroleum sulfonate, a mixture of sodium resinate, sodium naphthanate and sodium petroleum sulfonate and a mixture of guanidine stearate and triethanolamine stearate are particularly useful. It is usual to have a total emulsifier concentration of between about 10% and about 20% by weight of the cutting oil concentrate, exclusive of water, with concentrations between 12% and 16% ordinarily being employed.

Typical coupling agents include mono and polyhydroxy alcohols, ether-alcohols and phenols. Examples of these compounds include ethyl, isopropyl, n-propyl, isobutyl, n-butyl and n-amyl alcohols; ethylene glycol, diethylene glycol and propylene glycol, ethylene glycol alkyl ethers wherein the alkyl group has from 1 to 8 carbon atoms, for example ethylene glycol monoethylether (Cellosolve), ethylene glycol monoisopropylether, ethylene glycol monobutylether, ethylene glycol mono-n-pentylether, ethylene glycol mono-n-hexylether, diethylene glycol monoethylether (Carbitol), diethylene glycol monobutylether and cresol. The concentration of the coupling agent in the cutting oil concentrate, exclusive of water, usually is between about 0.1% and about 1.5% by weight. A particularly good coupling agent used in the cutting oil art is Cellosolve in a concentration of between about 0.6% and about 1% by weight of the cutting oil concentrate exclusive of the water.

A typical amount of water in the emulsion is about 70% by weight of the cutting oil.

Another use of the alkanolamide borates of the instant invention is as a rust-inhibitor, lubricative-enhancive addenda and bactericide/fungicide in a hydraulic fluid. The amount used is about the same as the amount used for a cutting oil. An effective range is from about 0.075% by wieght to about 1% by weight of the hydraulic fluid. Inasmuch as the constitutions of hydraulic fluids are well known and form the subject of many patents and publications, it merely will be mentioned here that a typical hydraulic fluid is anhydrous and includes a mineral oil and surfactants, a typical surfactant being a petroleum sulfonate. Examples of petroleum sulfonates useful for this purpose are the Petronates and Di-Petronates made by Sonneborn Division of Witco Chemical Company, Inc., and the Petrosuls manufactured by Pennsylvania Refining Co. Typical such petroleum sulfonates are Petronate L, Petronate HL, Petronate K, Petronate CR, Di-Petronate L, Di-Petronate HL, Di-Petronate K, Di-Petronate Cr, Petrosul 742, Petrosul 745, Petrosul 454, Petrosul 750, Petrosul 550 and Petrosul 744LC. A typical amount of petroleum sulfonate for use in a hydraulic fluid is 5% by wieght. Also useful as surfactants in hydraulic fluids are the emulsifying agents mentioned about in connection with cutting oil emulsion. A typical amount of such an emulsifying agent for use in a hydraulic fluid is 5% by weight.

The hydraulic fluids also may include water, the mix being about 60% by weight of the oil and emulsifying agent and about 40% by weight of water. The emulsion may be of the water-in-oil type or oil-in-water type. It will be appreciated that the foregoing is simply by way of example. Some hydraulic fluids constitute natural oils. Many hydraulic fluids do not include natural oils but are formulated from synthetic lubricants. Frequently, and particularly in the case of low temperature usages, these fluids are anhydrous. When the hydraulic fluids are anhydrous the alkanolamide borates employed likewise should be anhydrous.

The following are examples of anhydrous hydraulic fluids to which the alkanolamide borates of the instant invention are added in the amounts above indicated.

EXAMPLE 1

| Mineral oil base | Parts by weight |
|---|---|
| High viscosity mineral oil (S.U.S. 300) | 75 |
| Low viscosity mineral oil (S.U.S. 75) | 25 |
| Adjust to 160"/100° F. S.U.S. | |

EXAMPLE 2

| Mineral oil base | |
|---|---|
| High viscosity mineral oil (S.U.S. 300) | 70 |
| TEREGITOL 350* oleyl ester | 5 |
| Low viscosity mineral oil (S.U.S. 75) | 25 |
| Adjust to 160"/100° F.–180"/100° F. S.U.S. | |

*TEREGITOL 350 is a compound sold by Union Carbide which is an ethoxylated methanol (8 moles ethylene oxide) molecular weight 350.

EXAMPLE 3

| Mineral oil base | |
|---|---|
| Dipropylene glycol phosphate ester | 10 |
| High viscosity mineral oil (S.U.S. 300) | 60 |
| Triethanolamine | 5 |
| Low viscosity mineral oil | 25 |
| Adjust to 160"/100° F.–180"/100° F. S.U.S. | |

EXAMPLE 4

| Synthetic oil | |
|---|---|
| Propylene glycol phosphate | 60 |
| Triethanolamine | 30 |
| Propylene glycol | 10 |
| Adjust to 100"/100° F.–180"/100° F. S.U.S. | |

EXAMPLE 5

| Synthetic oil | |
|---|---|
| CARBOWAX 200* phosphate | 65 |
| Triethanolamine | 25 |
| Diethylene glycol | 10 |
| Adjust to 160"/100° F.–180"/100° F. S.U.S. | |

*CARBOWAX 200 is a compound sold by Union Carbide. It is an ethoxylated ethylene glycol (3.5. moles ethylene oxide) molecular weight 200.

Another use to which the alkanolamide borates of the instnat invention can be put is as a rust-inhibitor and inhibitor of mold growth for paints and varnishes where from 0.1% to about 5% by weight can be used by incorporating the borate into an otherwise conventional paint. Inasmuch as said borates are both oil and water soluble they can be incorporated in any kind of paint, being inert to the constituents of paint. Typical paints into which the said borates can be incorporated are water-base emulsion paints, such as acrylic paints, vinyl paints, latex paints and alkyd paints and oil-base paints such, for instance, as linseed oil paint.

As noted previously the alkanolamide borates which are the subject of the present invention, also can be added to synthetic and semi-synthetic oils which are used for many purposes and to extreme pressure lubricants. Synthetic oils are oils which are free of natural oil; semi-synthetic oils are oils containing water soluble oils such as polyglycol esters and sulfated or sulfonated oils. Extreme pressure lubricants contain additives that enable them to be used for high pressure purposes such as, for instance, high pressure grinding. These additives typically are chlorinated and sulfurized oils.

It will be appreciated that when the alkanolamide borates of the present invention are added to various liquid carriers for use as a rust-inhibitor or as a lubricative-enhancive addendum there must be present an amount which is functionally effective for the foregoing purposes that have been mentioned previously; such amount ranges between about 0.05% to about 5% to about 5% of the weight of the composition in which it is present.

It thus will be seen that there are provided alkanolamide borates, compositions containing the same and methods for making and using the same, which achieve the various objects of this invention and which are well adapted to meet the conditions of practical use.

As various possible embodiments might be made of the above invention, and as various changes might be made in the embodiments above set forth, it is to be understood that all matter herein described is to be interpreted as illustrative and not in a limiting sense.

Having thus described the invention there is claimed as new and desired to be secured by Letters Patent:

1. A composition comprising a liquid carrier constituting a hydraulic fluid base on mineral oils, water-in-oil emulsions, oil-in-water emulsions, and synthetic lubricating oil and a rust-inhibiting-effective amount of the reaction product of orthoboric acid and a primary alkanolamine selected from the group consisting of monoethanolamine, monomethanolamine, 1-isopropanolamine, mono-n-propanolamine and 2-amino-2-methylpropanolamine in a ratio of 1 gram mole of boric acid to 1 to 2 gram moles of alkanolamine, the reaction taking place in a closed reactor for about 4 to 5 hours at a temperature between about 130° C. to about 165° C. with the water formed being removed during the reaction.

* * * * *